United States Patent [19]

August et al.

[11] 4,250,301

[45] Feb. 10, 1981

[54] ANOMER ENRICHMENT OF ALKYL GLYCOSIDES OF AMINO SUGARS

[75] Inventors: Paul R. August, Wilmington; George A. Reed, Middletown, both of Del.

[73] Assignee: University of Delaware, Newark, Del.

[21] Appl. No.: 78,660

[22] Filed: Sep. 24, 1979

[51] Int. Cl.³ .................... C07H 15/04; C07H 5/06
[52] U.S. Cl. ..................................... 536/4; 536/18; 536/120
[58] Field of Search .................... 536/4, 1, 120, 18

[56] References Cited

U.S. PATENT DOCUMENTS 4,057,684 11/1977 Kimura et al. .................... 536/53
4,152,513 5/1979 Austin et al. .................... 536/4

Primary Examiner—Johnnie R. Brown

[57] ABSTRACT

Process for enrichment of β-anomers of alkyl glycosides of amino sugars involving two steps. The first step comprises treating an equilibrium mixture of the α- and β-anomers of the alkyl glycosides with an inorganic base under controlled reaction conditions, e.g., specific solvents, water content of solvent and temperature and time of treatment. These conditions cause the equilibrium to shift in favor of the β-anomer. The second step comprises subjecting the product of the first step to multiple fractionations in specific solvent mixtures to isolate products having increased proportions of the β-anomers of the alkyl glycosides of amino sugars.

5 Claims, No Drawings

ANOMER ENRICHMENT OF ALKYL GLYCOSIDES OF AMINO SUGARS

BACKGROUND OF THE INVENTION

The Government of the United States has rights in this invention pursuant to Grant No. 04-6-158-44025 from the Department of Commerce.

FIELD OF THE INVENTION

This invention relates to a method for preparing specific anomers of alkyl glycosides of amino sugars, also called, for example with glucosamine, the alkyl glucosaminides.

DESCRIPTION OF THE PRIOR ART

A process for the preparation of alkyl glycosides of amino sugars which enhances the formation of the β-anomers is described in U.S. Pat. No. 4,152,513, to Paul R. Austin and George A. Reed. This patent discusses the previously known methods for the preparation of these alkyl glycosides which gave products in which the α-anomer predominated. As pointed out by Austin and Reed the α-anomers of alkyl glycosides of amino sugars are more effective than α-anomers in many biological and pharmaceutical applications, and their process gives products having improved proportions of the β-anomer. Accordingly, it is desirable to employ anomers of alkyl glycosides of amino sugars having the highest possible β-anomer content.

It is therefore the primary object of this invention to provide a process for the enrichment of the β-anomers in the complex chiral α- and β-anomers of alkyl glycosides of amino sugars.

SUMMARY OF THE INVENTION

The process of this invention involves two steps in a cyclic system. In one step a mixture of the α- and β-anomers of an alkyl glycoside of an amino sugar high in α-anomer content and optical rotation is dissolved in an alcohol solution of an inorganic base containing a minor amount of water. This solution is maintained at a temperature of 20° to 60° C. until there is no further decrease in the optical rotation of the reaction solution. At this point the maximum inversion of α-anomer to β-anomer has occurred. The reaction solution is then cooled slowly to precipitate a mixture of the α- and β-anomers in which the proportion of β-anomer has been increased significantly.

The product of this step is dissolved at elevated temperature in a solvent consisting of a mixture of an aliphatic alcohol having 1-4 carbon atoms with an ester of an aliphatic alcohol and an aliphatic carboxylic acid, the ester having a maximum of 5 carbon atoms, and the ratio of the alcohol to the ester being between 20:80 and 50:50 by volume. The resulting solution, after filtering to remove insoluble material, is cooled slowly to a temperature of 0°–25° C. to crystallize out a mixture of α- and β-anomers of the alkyl glycoside of amino sugar in which the proportion of β-anomer is still further increased. The filtrate from this crystallization is heated and concentrated to about 70% of its original volume and then cooled slowly to 0°–25° C. to crystallize out a second crop of the alkyl glycoside. Each of these crops of alkyl glycoside crystals is then subjected to further solution and crystallization steps to concentrate in the first fractions greater proportions of the β-anomers. The residues from the multiple crystallizations contain higher proportions of the α-anomers and these can be combined and subjected to the basic alcohol inversion process of the first step of this invention. The resulting inversion product can then be subjected to the fractional crystallization process of the second step of this invention as outlined above.

The alkyl glycosides of amino sugars used in the process of this invention can be made by conventional methods such as, for example, by the method described by Paul R. Austin and George A. Reed in U.S. Pat. No. 4,152,513. The products of such processes are mixtures of chiral anomers in which the α-anomer predominates. For example, in the ethyl glycoside of N-acetylglucosamine the ratios of α- to β-anomers range from 55:45 to 81:19. Specific examples of such alkyl glycosides that are operable in this invention include: 1-propyl N-acetyl-D-glucosaminide, ethyl N-propionyl-D-glucosaminide, ethyl N-1-butyryl-D-glucosaminide, methyl N-acetyl-D-glucosaminide, 2-propyl N-propionyl-D-glucosaminide, ethyl N-acetyl-D-mannosaminide, and ethyl N-acetyl-D-galactosaminide. All of these sugar derivatives have the acylamino group in the C-2 position.

The alcohol used as solvent in the first step of this invention is an aliphatic alcohol having 1 to 4 carbon atoms, i.e., methanol, ethanol, 1-propanol, 2-propanol, 1-butanol, 2-butanol, and 2-methyl-2-propanol. The alcohol chosen as solvent preferably should have the same number of carbon atoms as the alkyl group in the alkyl glycoside being treated.

Inorganic bases useful in the inversion step of this invention include ammonia and the alkali metal hydroxides, e.g., lithium hydroxide, sodium hydroxide, and potassium hydroxide. The amounts of these bases that are used are those sufficient to produce alcoholic solutions ranging from 0.1 to 1.0 molar with respect to the base.

It is essential that the alcohol solvent contain a small amount of water, i.e., from 0.1% to 5.0% of water. The water can be provided by the use of 95% alcohol, or the desired amount of water can be added to absolute alcohol. When ammonia is used as the inorganic base in the inversion step, concentrated ammonium hydroxide can be used to provide both the ammonia and the water. When an alkali metal hydroxide is used, the commercially available hydroxide has sufficient water absorbed on the solid hydroxide to provide the water required in the inversion process.

The equilibrium mixture of the α- and β-anomers from ammonium hydroxide systems is isolated from the reaction mixture by removal of the solvent and ammonia by conventional means. Thus the alcohol can be removed by distillation at atmospheric or reduced pressure. Alternatively the alcohol and ammonia can be removed by passing a stream of air at ordinary or elevated temperature over the solution until a dry residue is obtained. When an alkali metal hydroxide is used it must be removed by treatment of the solution with an acid ion exchange resin prior to evaporation of the alcohol.

The temperature at which the inversion step is conducted can vary from about 20° to 60° C. The particular temperature used depends on the particular base being used and its concentration. The preferred temperatures are from 40° to 60° C. since at these temperatures substantial inversion of α-anomer to β-anomer takes place in 1–2 days, while at room temperature, 20°–30° C., times of up to one month are required.

The solvent mixture employed in the recrystallization step of this invention is a mixture of an aliphatic alcohol having 1–4 carbon atoms and an ester of an aliphatic alcohol with an aliphatic carboxylic acid, the ester having a maximum of 5 carbon atoms. Examples of suitable alcohols include methanol, ethanol, 1-propanol, 2-propanol, 1-butanol, 2-butanol and 2-methyl-2-propanol. Specific esters that can be used include methyl butyrate, ethyl acetate, 1-propyl acetate, 2-propyl acetate, 2-propyl formate, methyl propionate, and ethyl formate. As indicated above, the ratios of the alcohol to the ester in the recrystallization step of this invention range from 20:80 to 50:50.

In this recrystallization a complex appears to be formed between the glycoside and solvent, which is the product that precipitates and is recovered. Subsequent drying removes this complexed solvent and yields a friable, well-crystallized powder.

The ratios of the $\alpha$- and $\beta$-anomers in the alkyl glycosides of amino sugars formed in the process of this invention are readily calculated from the measured optical rotations of the products and the optical rotations of known pure $\alpha$- and $\beta$-anomers. This method is described in U.S. Pat. No. 4,152,513.

DETAILED DESCRIPTION OF THE PREFERRED EMBODIMENTS

The best modes contemplated for carrying out the process of this invention are illustrated by the following examples:

EXAMPLE I

Ten ml of a 0.25 molar (M) solution of ethyl N-acetylglucosaminide in absolute ethyl alcohol and 15 ml of 1.67 molar (M) aqueous ammonium hydroxide (approximately 6 M with respect to water) are placed in a 25 ml volumetric flask and absolute ethyl alcohol is then added to make 25 ml of solution which is 0.1 M with respect to the ethyl N-acetyl glucosaminide, 1.0 M with respect to ammonia and 4 M with respect to water (or in other terms the solution contains 3.4% water). The observed optical rotation, $\theta$, immediately after mixing the ingredients is 5.2, which corresponds to $[\alpha]_D = +100°$. This value indicates an $\alpha$-/$\beta$-anomer ratio of 81/19. The basic solution is placed in a water bath maintained at a temperature of 53° C.±3° for 24 hours. At the end of this period $\theta$ is found to be 4.0, which corresponds to $[\alpha]_D = +76°$, which in turn indicates an $\alpha$-/$\beta$-anomer ratio of 67/33. No further change in $\theta$ occurs during storage at 53° C. for another 24 hours.

EXAMPLE II

Another 25 ml solution of ethyl N-acetylglucosaminide (0.1 M) in ammoniacal ethyl alcohol is made up in the same manner as described in Example I except that the ammonia concentration is 0.1 M and the water concentration is 0.4 M (or 0.34%). The optical rotation, $\theta$, of the freshly prepared solution is 5.2. After 24 hours at 53° C.±3° the solution has a value of $\theta = 4.2$. This corresponds to $[\alpha]_D = +80°$, which indicates the $\alpha$-/$\beta$-anomer to be 70/30. The original ratio was 83/17.

EXAMPLE III

Ten ml of a 0.25 M solution of ethyl N-acetylglucosaminide in absolute ethyl alcohol and 1.0 g of sodium hydroxide are placed in a 25 ml volumetric flask and absolute ethyl alcohol is added to make 25 ml of solution which is 0.1 M with respect to the ethyl glycoside, 1.0 M with respect to sodium hydroxide, and approximately 0.1 M with respect to water (which was absorbed on the solid sodium hydroxide). The observed optical activity, $\theta$, of the freshly prepared solution is 5.2, which corresponds to $[\alpha]_D = +100°$ and to an $\alpha$-/$\beta$-anomer ratio of 81/19. The test solution is maintained at a temperature of 53° C.±3° for 24 hours. At the end of this period the solution has a $\theta$ value of 3.8, which corresponds to $[\alpha]_D = +72°$ and an $\alpha$-/$\beta$-anomer ratio of 65/35. The reaction solution darkens to some extent during this treatment.

EXAMPLE IV

In this example a 0.1 M solution of ethyl N-acetylglucosaminide in ethyl alcohol is made up in the manner described in Example III with the exception that the solution is 0.1 M with respect to sodium hydroxide and 0.1 M with respect to water. As in Example III the optical activity of the freshly prepared solution is 5.2, corresponding to $[\alpha]_D = +100°$, and to $\alpha$-/$\beta$-anomer ratio of 83/17. The solution is maintained at 53° C.±3° for 24 hours. The solution is then found to have $\theta = 4.1$, which corresponds to $[\alpha]_D = 78°$, and the $\alpha$-/$\beta$-anomer ratio is 68/32. As in Example III the reaction solution darkens, but to a lesser degree than in that example.

EXAMPLE V

Five grams of ethyl N-acetylglucosaminide having $[\alpha]_D = +53°$ (indicating an $\alpha$-/$\beta$-anomer ratio of 54/46) is dissolved in a mixture of 20 ml of isopropyl alcohol and 80 ml of ethyl acetate at its boiling point. The hot solution is filtered to remove insoluble material and the filtrate is cooled slowly to room temperature and then held at 0°–5° C. for 72 hours. The very fine white crystals that form are filtered out and, after air drying, amount to 2.4 g. These crystals have $[\alpha]_D = +47°$, which corresponds to an $\alpha$-/$\beta$-anomer ratio of 50/50. Two grams of these crystals are then dissolved in a mixture of 12 ml of isopropyl alcohol and 18 ml of ethyl acetate at the boiling point and the mixture filtered while hot. The filtrate is slowly cooled to 0°–5° C. (during a period of 5 hours) and held at that temperature for another 20 hours. The crystals obtained on this second recrystallization amount to 0.99 g and have $[\alpha]_D = +25°$, which corresponds to an $\alpha$-/$\beta$-anomer ratio of 38/62.

EXAMPLE VI

Ten grams of ethyl N-acetylglucosaminide having an $\alpha$-/$\beta$-anomer ratio of 54/46 is dissolved in a mixture of 60 ml of 95% ethyl alcohol and 140 ml of ethyl acetate at its boiling point. The hot solution is filtered, and the filtrate is cooled slowly in a water bath to 0°–5° C. The crystals that form are filtered out, washed with 75 ml of cold ethyl alcoholethyl acetate (70-30) solvent and air dried on filter paper for two days. These crystals amount to 2.3 g and have $[\alpha]_D = +30°$, which corresponds to an $\alpha$-/$\beta$-anomer ratio of 41/59. The filtrate from this crystallization, 140 ml, is again heated and the solvent evaporated until the volume reaches 100 ml whereupon it is again cooled slowly to 0°–5° C. This crop of crystals after drying, amounts to 3.9 g with $[\alpha]_D = +65°$, which corresponds to an $\alpha$-/$\beta$-anomer ratio of 61/39.

EXAMPLE VII

Twenty grams of ethyl N-acetyl glucosaminide, having an $\alpha/\beta$ ratio of 55/45, is dissolved in a mixture of 105 ml isopropyl alcohol and 245 ml ethyl acetate at the boiling point of the mixture. The hot solution is filtered and allowed to cool in an insulated beaker to room temperature, the process taking about four hours. The crystals that form are filtered out, washed with 100 ml ethyl acetate and air-dried for 24 hours. These crystals weigh 10.9 grams, having $[\alpha]_D = +45°$ and an $\alpha/\beta$ ratio of 50/50. The filtrate from this crystallization is evaporated to dryness leaving a residue of 8.1 g with an $[\alpha]_D = +66°$, corresponding to an $\alpha/\beta$ ratio of 61/39.

The initial fraction described above is again recrystallized by the same procedure, giving 5.4 g of crystals with $[\alpha]_D = +31°$ and an $\alpha/\beta$ ratio of 42/58.

The twice recrystallized products from three trials carried out in identical manner are combined (total weight of 23.5 g) and are recrystallized from 105 ml isopropyl alcohol and 245 ml ethyl acetate, giving 17.2 g crystals with $[\alpha]_D = +25°$ and an $\alpha/\beta$ ratio of 38/62. Repeated recrystallization of this material results in crystals with $[\alpha]_D = +5°$ and an $\alpha/\beta$ ratio of 27/73.

The combined residues obtained from the filtrates of three crystallizations carried out as described in the first paragraph of this Example amounting to 25 g and having an $[\alpha]_D$ of $+66°$ are twice recrystallized in the same manner and yield crystals having an $[\alpha]_D$ of $+58°$ and $+69°$, respectively. The residue from the second recrystallization has an $[\alpha]_D$ of $88°$, which corresponds to an $\alpha$-/$\beta$-anomer ratio of 74/26. A 2.49 g portion of this last residue is dissolved in absolute ethanol and placed in a 100 ml volumetric flask with 50 ml of 6 N $NH_3$ (alcoholic) and 3 ml $H_2O$ and the entire mixture diluted to 100 ml with ethanol. The resulting solution is 3 M with respect to $NH_3$, 0.1 M with respect to the glycoside and contains 3% $H_2O$ by volume. This solution is then placed in a constant temperature bath held at 50° C. for 48 hours. During this time, the $[\alpha]_D$ falls to $+70°$, corresponding to an $\alpha/\beta$ ratio of 64/36. The solution is evaporated under a stream of air to remove the $NH_3$ and the solvent. The resulting solid is washed with 25 ml methyl ethyl ketone to remove any yellowish discoloration. The resulting solid (2.0 g) has an $[\alpha]_D$ of $+80°$, corresponding to an $\alpha/\beta$ ratio of 69/31.

The alkyl glycosides of amino sugars obtained by the process of this invention are especially useful as growth promoters for *L. bifidus*, since it is known that the $\beta$-anomers of the alkyl glycosides of amino sugars are more active promoters than the $\alpha$-anomers, and since this process produces higher proportions of the more desirable $\beta$-anomers. Mixtures of different alkyl glycosides of amino sugars are also useful as growth promoters for *L. bifidus*. For example, addition of the $\alpha$-anomer of methyl-D-glucosaminide to the $\beta$-anomer of methyl-D-glycosamide or to the $\beta$-anomer of higher alkyl-D-glucosaminides enhances the activity of these alkyl glycosides for this purpose.

In addition to their usefulness as growth promoters for *L. bifidus*, the alkyl glycosides of amino sugars are also useful in promoting the healing of wounds. For example, they can be used in treatment of burns, skin inflammation, and psoriasis. They also can be used as promoters of *L. bifidus* growth for use in the treatment of liver disorder. Another use for the alkyl glycosides of amino sugars is for application to hair to control its growth.

It is apparent that changes and modifications may be made without departing from the invention in its broader aspects. The aim of the appended claims, therefore, is to cover all such changes and modifications as fall within the true spirit and scope of the invention.

I claim:

1. The process for the enrichment of $\beta$-anomers in an equilibrium mixture of $\alpha$- and $\beta$-anomers of alkyl glycosides of amino sugars which comprises subjecting an alcoholic solution of such anomers, containing an inorganic base and 0.1 to 5.0% water based on the alcohol content of the solution, to a temperature of 20°–60° C. until there is no further decrease in the optical activity of the solution; then dissolving the anomer product of this step in a solvent consisting of a mixture of an aliphatic alcohol having 1–4 carbon atoms with an ester of an aliphatic alcohol and an aliphatic carboxylic acid, the ester having a maximum of 5 carbon atoms and the ratio of the alcohol to the ester being between 20:80 and 50:50 by volume, at a temperature up to the boiling point of the solution, then cooling the solution slowly to 0°–25° C. to crystallize out a mixture of the $\alpha$- and $\beta$-anomers in which the proportions of $\beta$-anomer is still further increased.

2. The process of claim 1 in which the aliphatic alcohol used as solvent has 1–4 carbon atoms, and the solution is 0.1 to 1.0 molar with respect to the inorganic base.

3. The process of claim 2 in which the inorganic base is ammonia or an alkali metal hydroxide.

4. The process for the enrichment of $\beta$-anomers in an equilibrium mixture of $\alpha$- and $\beta$-anomers of alkyl glycosides of amino sugars which comprises subjecting an aliphatic alcoholic solution of the mixture of said anomers containing an inorganic base and 0.1 to 5% water based on the alcohol content of the solution, to a temperature of 20°–60° C. until there is no further decrease in the optical activity of the solution.

5. The process for the enrichment of $\beta$-anomers in a mixture of $\alpha$- and $\beta$-anomers of alkyl glycosides of amino sugars which comprises dissolving a mixture of said anomers in solvent consisting of a mixture of an aliphatic alcohol having 1–4 carbon atoms with an ester of an aliphatic alcohol and an aliphatic carboxylic acid, the said ester having a maximum of 5 carbon atoms, and the ratio of the alcohol to the ester being between 20:80 and 50:50 by volume, at a temperature up to the boiling point of the solution, then cooling the solution slowly to 0°–25° C. to crystallize out a mixture of $\alpha$- and $\beta$-anomers in which the proportion of $\beta$-anomers is still further increased.

* * * * *

UNITED STATES PATENT AND TRADEMARK OFFICE
CERTIFICATE OF CORRECTION

PATENT NO. : 4,250,301
DATED : February 10, 1981
INVENTOR(S) : Paul R. Austin

It is certified that error appears in the above—identified patent and that said Letters Patent is hereby corrected as shown below:

On the title page, Item [75] "August" should read -- Austin --.

Signed and Sealed this

Thirtieth Day of June 1981

[SEAL]

Attest:

RENE D. TEGTMEYER

Attesting Officer

Acting Commissioner of Patents and Trademarks